United States Patent
Macklem et al.

[11] Patent Number: 6,074,350
[45] Date of Patent: Jun. 13, 2000

[54] MEASUREMENT OF AIRWAY CALIBRE

[75] Inventors: Peter Tiffany Macklem, Montreal, Canada; Christopher Kenyon, Birmingham, United Kingdom; Anne Vezina, Toronto, Canada; Geoffrey Maksym, Boston, Mass.

[73] Assignee: McGill University, Montreal, Canada

[21] Appl. No.: 09/047,398

[22] Filed: Feb. 25, 1998

[30] Foreign Application Priority Data

Mar. 26, 1997 [CA] Canada ................................ 2201042

[51] Int. Cl.[7] ............................................. A61N 5/00

[52] U.S. Cl. ................................. 600/532; 600/529

[58] Field of Search .................... 600/532–538; 128/897–899

[56] References Cited

U.S. PATENT DOCUMENTS

| | | | |
|---|---|---|---|
| 4,220,161 | 9/1980 | Berlin et al. | 600/533 |
| 5,233,998 | 8/1993 | Chowienczyk et al. | 600/533 |
| 5,320,108 | 6/1994 | Cloutier | 600/529 |
| 5,522,397 | 6/1996 | Vermaak | 600/533 |

*Primary Examiner*—Cary O'Connor
*Assistant Examiner*—Michael Astorino
*Attorney, Agent, or Firm*—Swabey Ogilvy Renault

[57] ABSTRACT

The variation in flow resistance of the respiratory system (Rrs) is determined as an indicator of variations in airway calibre, by oscillating the system, for example at 6 Hz for 5–15 minutes and determining the variations in ratio of the pressure difference (Prs) across the system that is in phase with flow, to flow $\dot{V}$. The variation in airway calibre may be employed as a prognostic indicator in asthmatics and also to assess the efficacy of treatment.

11 Claims, 3 Drawing Sheets

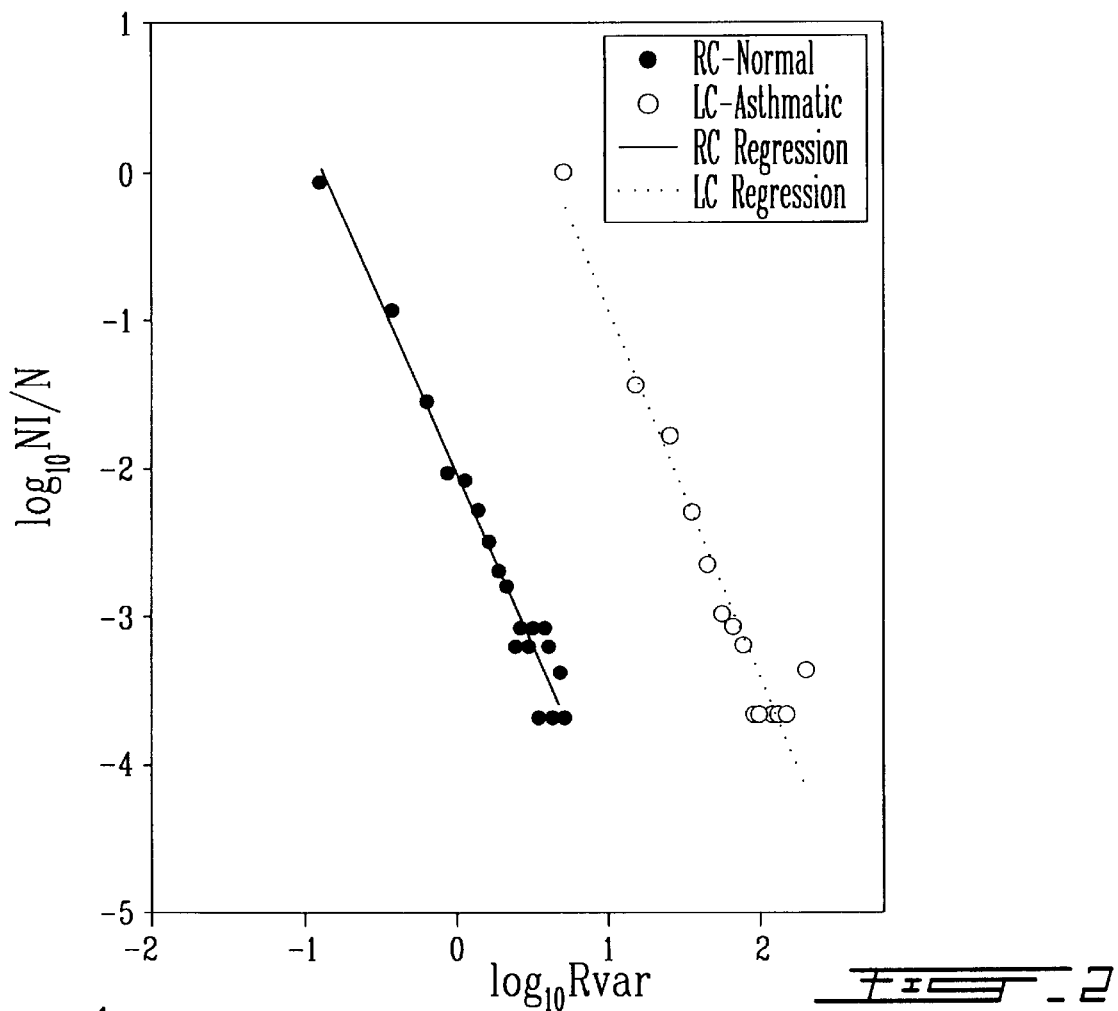
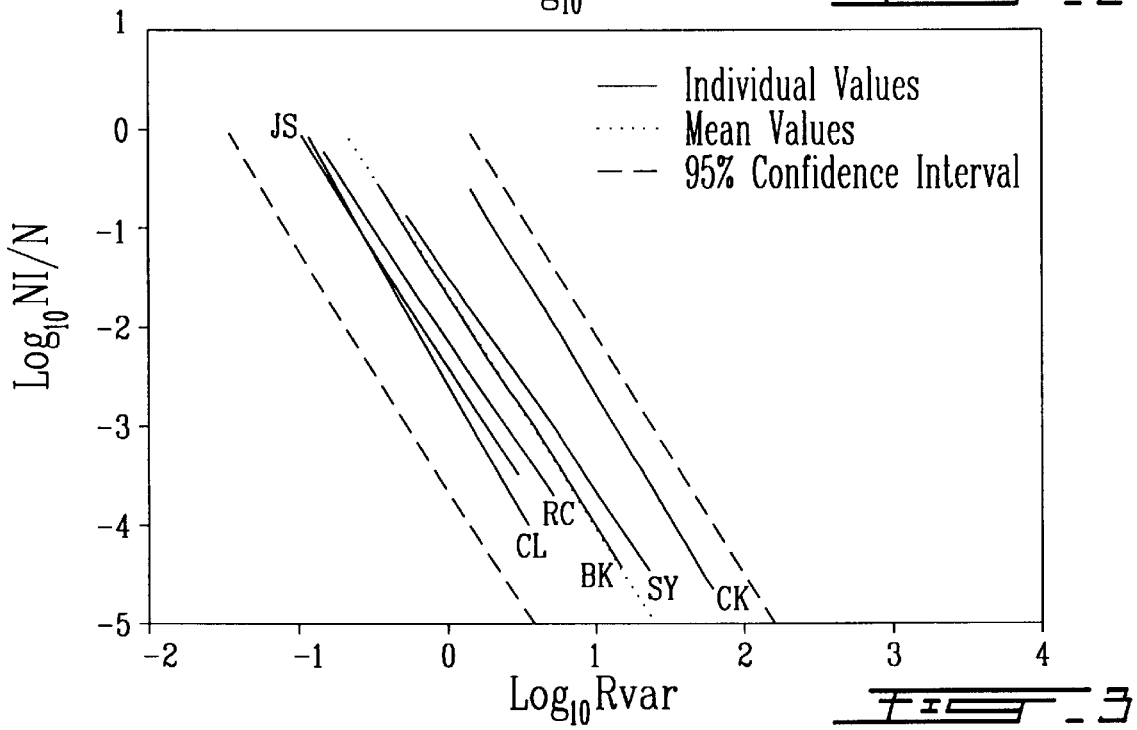

MEASUREMENT OF AIRWAY CALIBRE

BACKGROUND OF THE INVENTION

This invention relates to a method and apparatus for determining variation in the airway calibre of a respiratory system.

It is appropriate to monitor the respiratory system of asthmatics to assess the efficacy of treatment being carried out and to assess the likelihood of a life-threatening event.

Existing monitoring techniques include peak expiratory flow measurements employed by asthmatics in self-monitoring in the home, however, this technique requires the use of special breathing maneuvers which have to be learned by the subject.

SUMMARY OF THE INVENTION

In accordance with the present invention the flow-resistance of the respiratory system, (Rrs) is employed as an index of airway calibre. This measurement is obtained by oscillating the respiratory system by an external device and plotting the ratio of the pressure difference across the system that is in phase with flow (Prs;=mouth pressure–body surface or atmospheric pressure) to flow ($\dot{V}$). Thus: Rrs=Prs/$\dot{V}$.

Although this measurement includes the resistance of the lung parenchyma and the chest wall, variations in Rrs with time are assumed to be due primarily to variations in airway calibre.

In accordance with one aspect of the invention this is provided a method of determining airway calibre of a respiratory system comprising oscillating the respiratory system, during breathing, by an external oscillating means to establish a flow of breathing air having superimposed oscillations, determining a component of pressure Prs in phase with said flow, determining the flow rate $\dot{V}$, and computing the flow resistance Rrs from the ratio Prs/$\dot{V}$ as a measure of airway calibre.

In an embodiment of this method values of Prs and $\dot{V}$ are determined repeatedly over a defined period and the frequency distribution of variations Rvar in Rrs with time is computed as a signal of spontaneous variation in airway calibre.

In a particular embodiment of the invention there is provided a method of determining airway calibre of a respiratory system in evaluation of respiratory system conditions comprising providing a breathing mouthpiece and a breathing zone of low resistance and high inertance, with a flow passage separating said breathing mouthpiece from said breathing zone, allowing breathing air to flow between said mouthpiece and said breathing zone along said flow passage, directing sinusoidal oscillations along said flow passage towards said mouthpiece, during said flow of breathing air, measuring air flow generated by the breathing with the sinusoidal oscillations superimposed thereon, in said flow passage, and developing a flow signal, measuring the pressure in said flow passage and developing a pressure difference signal, and computing flow resistance of the system from said flow signal and said pressure difference signal as a measure of airway calibre.

In a particular embodiment the flow resistance and pressure difference are determined repeatedly over a period of time and the frequency distribution of variations Rvar in Rrs with time is computed as a signal of spontaneous variation in airway calibre.

In an especially preferred embodiment the oscillating is at 6 Hz for 5 to 15 minutes.

In another embodiment of the invention there is provided apparatus for determining airway calibre of a respiratory system comprising a breathing mouthpiece and a breathing zone of low resistance and high inertance, with a flow passage separating said breathing mouthpiece from said breathing zone, means for generating sinusoidal oscillations in said flow passage, means for measuring flow $\dot{V}$ in said flow passage as a combination of breathing flow generated by breathing through said mouthpiece and the superimposed sinusoidal oscillations, means for measuring pressure in said flow passage, computing means for determining pressure Prs attributable to the flow and flow resistance Rrs as a ratio of Prs/$\dot{V}$.

In a particular embodiment the means for generating oscillations is adapted to develop oscillations of about 6 Hz, and the computing means is adapted to compute airway calibre over a period of time, for example 5 to 15 minutes so as to determine variations in airway calibre.

BRIEF DESCRIPTION OF DRAWING

FIG. 2 which shows a frequency distribution curve of log frequency versus log impedance variation for normal and asthmatic patients.

FIG. 3 shows linear regressions for normals and asthmatics on a graph of log frequency versus log impedance variation.

DESCRIPTION OF PREFERRED EMBODIMENT WITH REFERENCE TO DRAWING

Figure 1:
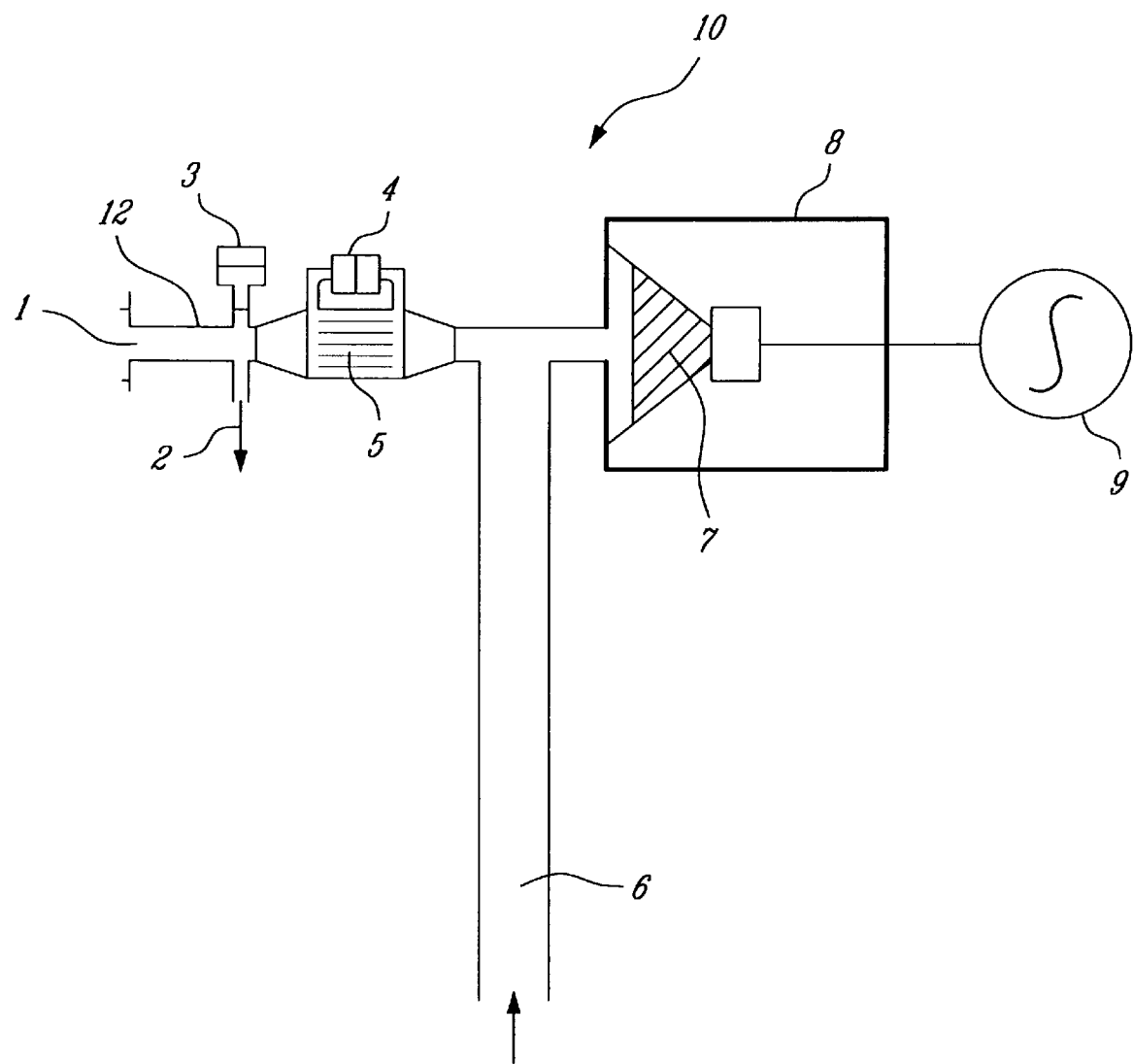
FIG. 1 is a schematic representation of apparatus of the invention for use in the method of the invention.

With reference to FIG. 1 there is shown apparatus 10. The subject breathes with a noseclip in place through a mouthpiece 1 in and out through breathing zone defined by a low resistance high inertance wide bore tube 6 from and to the room. A side port 2 in a flow passage defined by a tube 12 attached between the mouthpiece 1 and tube 6 is attached to a negative pressure source producing a continuous steady flow of air through 6 and out though 2 providing a continuous supply of fresh air to the subject breathing on the mouthpiece. A loudspeaker 7 enclosed in a box 8 and powered by a variable frequency sine wave generator 9 oscillates sinusoidally at 6 Hz. Because the tube 6 has a high inertance, the rapid 6 Hz oscillations do not enter the tube 6 but oscillate the subject producing a sinusoidally oscillating flow in and out of the lung in the flow passage defined by the tube 12. Because the tube 6 has low resistance the subject can easily breathe through it at normal breathing frequencies of~15/min. The flow ($\dot{V}$) generated by the subject's breathing, plus the superimposed sinusoidal oscillations produced by the loudspeaker 7 are measured in tube 12 by the flow meter 5 and its attached pressure transducer 4. A transducer 3 attached to the tube 12 at the mouthpiece measures pressure. The pressure and flow signals are passed through an A to D converter into a computer with software that computes the component of pressure that is in phase with flow and calculates $\nabla$Prs/$\nabla\dot{V}$=Rrs.

The subject breathes normally through the apparatus 10 for 5–15 minutes while Rrs is measured continuously at 6 Hz giving from 1800–5400 separate measurements of Rrs. When data collection is complete appropriate software rejects breaths when the subject is swallowing when Rrs→00 or when the subject comes off the mouthpiece when Rrs→0. When the data are cleared the software calculates the frequency distribution curve of the variation in Rrs over time as a signal of the spontaneous variation in airway calibre.

By calculating the variation of Rrs (Rvar) around the mean Rrs as a function of time the mean value of Rrs is subtracted from the instantaneous value and the result is squared to give 1800–5400 measurements of Rvar. Then Rvar is histogrammed into 20 bins spanning the range from minimum Rvar to maximum Rvar. Linear regression is used to obtain the best fit of log frequency to log Rvar and the slopes and intercepts are measured.

The data are describable by $E^b=1/f$ when E=power, f=frequency and b is the slope of the log f–log E plot. Correlation coefficients of the linear regression for all the plots varied between 0.90 and 0.99. The value of b was not significantly different between upright asthmatics and upright normals (mean±SEM: 3.09±0.21 vs 2.86±0.18, p>0.05) nor was it different in different postures and following methacholine in normal subjects (supine: 2.68±0.11; Mch: 3.31±0.42; Mch+supine: 2.99±0.39, p>0.05). However, in normal subjects the intercept was increased by the supine posture, by Mch and even more so by Mch supine. There was a dissociation between the magnitude of airway narrowing as measured by Rrs and variation in airway calibre over time measured by $E^b=1/f$. This was demonstrated by a lack of correlation between mean Rrs and the intercept.

In asthmatics the intercept on the x axis of the log f vs log E was significantly increased by as much as 2 log units. Because the slope of the plot was~–3, this suggests that some asthmatics undergo a given spontaneous variation in airway calibre $10^6$ times more frequently than normal subjects.

It appears that variation in airway calibre over time can be described and analyzed by 1/f noise and that asthmatics can be distinguished from normals by the difference in the intercept. The similarity of the slopes within and between subjects strongly suggests that airway smooth muscle is in a state of self-organized criticality.

An increase in intercept in asthma may represent an increase in risk for a large variation in airway calibre and thus a serious asthmatic attack, and that asthmatics with a higher intercept are at greater risk for a life-threatening event. Thus the intercept in asthma may be useful as a prognostic indicator, and also as a means to assess the efficacy of treating, as one of the treatment objectives would be to decrease the intercept.

The reference to the tube 6 having high inertance means that impedance to rapid accelerations of flow at the oscillating conditions, for example 6 Hz, is large, while being small to slower accelerations of flow, for example about 0.25 Hz, i.e. normal breathing frequency. As a consequence the patient can easily breathe through the tube 6, but the rapid oscillations do not pass through tube 6, but instead pass into the patient.

The device to measure the slope and intercept could easily be placed in an asthmatics home and no special breathing maneuvers are required by the subject to make the measurement (in contrast to peak expiratory flow measurement which is how asthmatics monitor their disease at home today). The data can easily be collected and analyzed on a microchip incorporated in the apparatus with an automatic readout for the patient or sent by telephone lines to a central computing and data bank facility which can then automatically send reports to the physician or clinic. Thus the apparatus may function as a home monitoring system largely replacing peak expiratory flow measurements.

PARTS OF FIG. 1

1. Mouthpiece.
2. Constant biased flow~7/min bringing continuous supply of fresh air in through tube 6 to the mouthpiece.
3. Pressure transducer measuring pressure difference across the respiratory system (mouth pressure 10 body surface pressure).
4. Pressure transducer to measure pressure drop across the flow-meter 5.
5. Flow-meter.
6. Low resistance, high inertance, long wide bore tubing.
7. Loudspeaker.
8. Box enclosing loudspeaker.
9. Variable frequency sine wave generator.
10. Apparatus.
12. Tube between mouthpiece 1 and tubing 6.

EXAMPLES

Experiments were performed on live human subjects in which total respiratory impedance was measured by 6 Hz forced oscillations while breathing quietly for 15 minutes in 10 seated asthmatics and 6 seated normals. Calculations were made of total impedance "Rrs". Individual values were subtracted from the mean, and squared to obtain Rrs variation "Rvar" to then plot log 10 transformations. The resulting values were then divided into bins with plots of their frequency distribution as log 10 Rvar versus log 10 frequency.

FIG. 2 shows frequency distribution curves for individual normal and asthmatic subjects. The distribution curves are plotted as log frequency versus log Rvar. These frequency distribution curves illustrate how the asthmatic patient has an intercept value on the log 10 Rvar axis which is distinct from the intercept value of the normal patient on the log 10 Rvar access.

FIG. 3 illustrates the plot of log frequency versus log Rvar for a number of normal and asthmatic subjects. Also plotted on this graph are the calculated mean values illustrated by a line of small dots. The 95% confidence interval is illustrated by sets of dashed lines.

Figure 4:
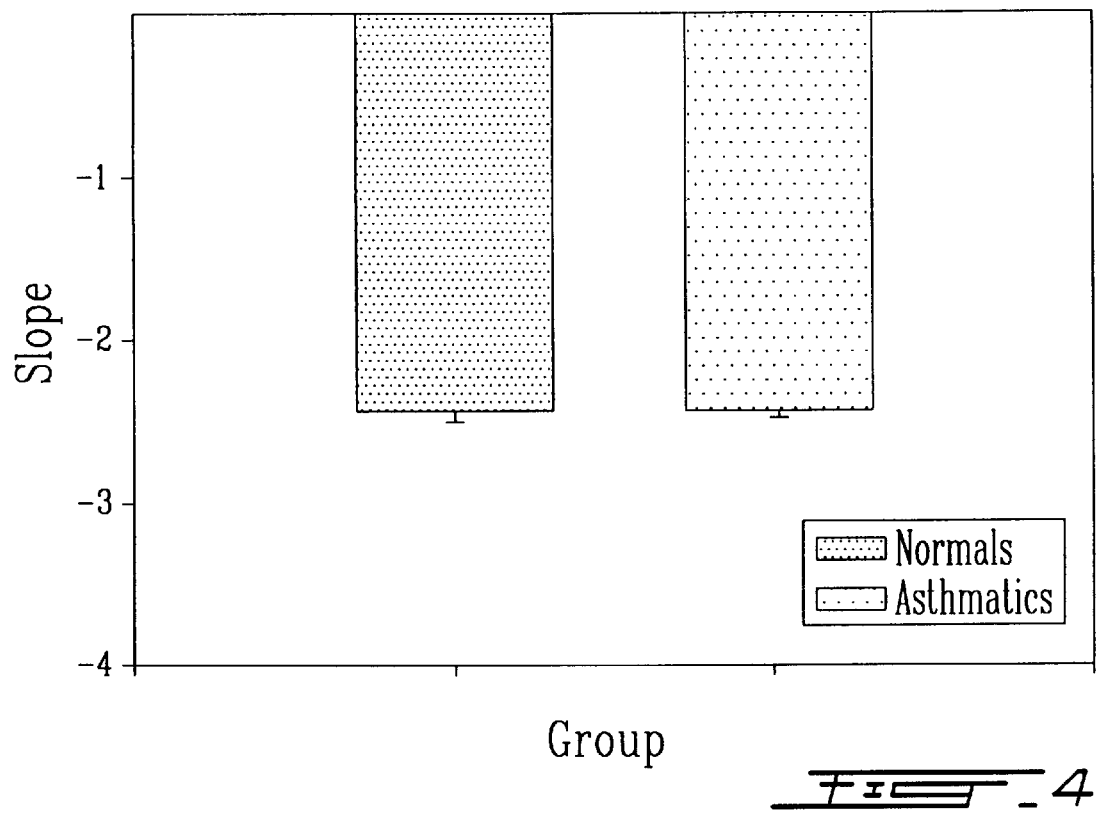
FIG. 4 shows a slope comparison between normals and asthmatics with graphical representations of slope versus group.

FIG. 4 illustrates a sloped comparison for groups of normals and asthmatics generated from the slopes of FIGS. 2 and 3. As can be seen in this illustration, no substantial difference exists between the slopes for normals and asthmatic subjects.

Figure 5:
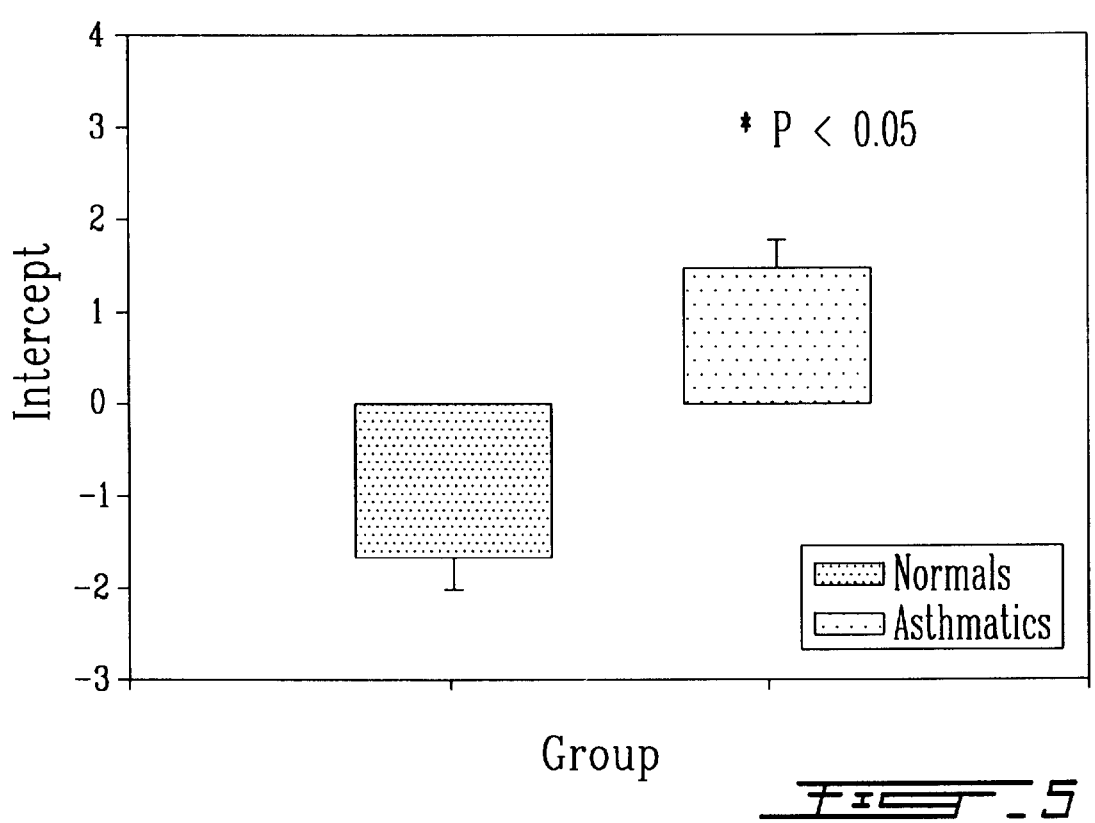
FIG. 5 shows an intercept comparison between normals and asthmatics and which illustrates the intercept comparisons between normals and asthmatics for each group.

FIG. 5 illustrates the range of intercept values plotted against individual groups of normal and asthmatic subjects. As can be readily appreciated from this Figure, the asthmatic subjects had intercept values that differed substantially from the intercept values of normal subjects.

The results of these plots demonstrate that Rvar follows a power law quantifiable by the equation of a straight line, and that the difference between asthmatics and normals can be quantified by single number. Furthermore, the plots show that Rvar might predict asthmatics at risk for serious attacks and access benefits for therapy. The Rvar is thus a useful number in medical diagnosis and thus has utility in the assessment of asthmatic patients.

We claim:

1. A method of determining spontaneous variation in airway calibre of a respiratory system comprising:

oscillating the respiratory system during breathing by an external oscillation means to establish a combined flow comprising a flow of breathing air having an oscillating flow of air superimposed on said flow of breathing air, determining a component of pressure Prs in phase with said combined flow, determining the flow rate V of said combined flow, computing the flow resistance Rrs of said combined flow from the ratio Prs/V as a measure of airway calibre, and determining values of Prs and V repeatedly over a defined period and computing the frequency distribution of variation Rvar in Rrs with time as a signal of spontaneous variation in airway calibre.

2. A method according to claim 1, wherein said oscillating is at about 6 Hz and said defined period is 5 to 15 minutes.

3. A method of determining spontaneous variation in airway calibre of a respiratory system in evaluation of respiratory system conditions comprising:

providing a breathing mouthpiece and a breathing zone of low resistance and high inertance, with a flow passage communicating said breathing mouthpiece with said breathing zone, allowing breathing air to flow between said mouthpiece and said breathing zone along said flow passage, directing sinusoidal oscillations along said flow passage towards said mouthpiece, during said flow of breathing air to form a combined flow comprising the flow of breathing air having a sinusoidal oscillating flow of air superimposed on the flow of breathing air, measuring the combined air flow generated by the breathing flow with the sinusoidal oscillations superimposed thereon, in said flow passage, and developing a flow signal, measuring the pressure in said flow passage and developing a pressure difference signal, computing flow resistance of the system from said flow signal and said pressure difference signal as a measure of airway calibre, and computing the frequency distribution of variation of said flow resistance with time from a multiplicity of values of the flow resistance over a defined period as a signal of spontaneous variation in airway calibre.

4. Apparatus for determining spontaneous variation in airway calibre of a respiratory system comprising:

a breathing mouthpiece and a breathing zone of low resistance and high inertance, with a flow passage communicating said breathing mouthpiece with said breathing zone, means for generating sinusoidal oscillations in said flow passage, means for measuring flow V in said flow passage as a combination of breathing flow generated by breathing through said mouthpiece, and the superimposed sinusoidal oscillations, means for measuring pressure in said flow passage, computing means for determining pressure Prs attributable to the flow and flow resistance Rrs as a ratio of Prs/V, and means for collecting a multiplicity of values of flow resistance Rrs over a defined period and for computing the frequency distribution of variation Rvar of the flow resistance Rrs with time, as a signal of spontaneous variation in airway calibre.

5. A method according to claim 1, wherein said flow of breathing air is at a normal breathing frequency of about 15/min.

6. A method according to claim 2, wherein said flow of breathing air is at a normal breathing frequency of about 15/min.

7. A method according to claim 2, wherein Prs and V are measured continuously over said defined period to produce 1800–5400 separate measurements of Rrs and Rvar is computed from said 1800–5400 separate measurements.

8. A method according to claim 3, wherein said flow of breathing air is at a normal breathing frequency of about 15/min.

9. A method according to claim 3, wherein said sinusoidal oscillations are developed by oscillating at about 6 Hz and said defined period is 5 to 15 minutes.

10. A method according to claim 8, wherein said sinusoidal oscillations are developed by oscillating at about 6 Hz and said defined period is 5 to 15 minutes.

11. A method according to claim 3, wherein said multiplicity of values is 1800–5400.

* * * * *